United States Patent [19]

Juodikis et al.

[11] Patent Number: 5,000,035
[45] Date of Patent: Mar. 19, 1991

[54] APPARATUS FOR MEASURING VAPOR PRESSURE

[75] Inventors: Peter Juodikis, Chicago; Clifford C. Johnson, Arlington Heights; Theodore Christie, Evanston, all of Ill.

[73] Assignee: Precision Scientific, Inc., Chicago, Ill.

[21] Appl. No.: 491,050

[22] Filed: Mar. 9, 1990

[51] Int. Cl.$^5$ .............................................. G01N 7/14
[52] U.S. Cl. .............................. 73/64.200; 73/29.030
[58] Field of Search .................... 73/64.2, 29, 29.03; 55/52

[56] References Cited

U.S. PATENT DOCUMENTS 4,543,819 10/1985 Chin et al. ........................... 73/64.2

FOREIGN PATENT DOCUMENTS 265553 6/1970 U.S.S.R. ................................ 73/64.2
505916 10/1976 U.S.S.R. ................................ 73/64.2

OTHER PUBLICATIONS

Herzog Reid, Semi-Automatic Vapor Pressure Apparatus brochure, unknown date of publication.
*Standard Test Method for Vapor Pressure of Petroleum Products*, (Reid Method), published Oct., 1982.

Primary Examiner—Hezron E. Williams
Assistant Examiner—Joseph W. Roskos
Attorney, Agent, or Firm—Emrich & Dithmar

[57] ABSTRACT

Apparatus for measuring the vapor pressure of a volatile liquid includes one or more cylindrical test chambers immersed in a constant temperature water bath. Each test chamber includes connected liquid and vapor compartments, with the vapor compartment coupled to a pressure transducer and display arrangement. The test chambers are mounted to a movable tray in the constant temperature water bath. An eccentric drive assembly driven by the combination of a motor and gear box is coupled to the tray for linearly displacing the tray and test chambers in a reciprocating manner until a constant pressure is observed on the pressure display.

13 Claims, 2 Drawing Sheets

APPARATUS FOR MEASURING VAPOR PRESSURE

FIELD OF THE INVENTION

The vapor pressure of a volatile liquid such as a petroleum product must meet manufacturing and environmental criteria. For example, petroleum products such as gasoline and crude oil have relatively high vapor pressures and tend to increase atmospheric pollution with noxious fumes. Other liquids having high vapor pressures may contaminate the atmosphere with particulate pollutants. In order to determine if the vapor pressure is within acceptable limits, it must be accurately measured. The present invention provides an improved arrangement for accurately measuring the vapor pressure of a volatile liquid such as gasoline.

BACKGROUND AND SUMMARY OF THE INVENTION

The Semiautomatic Reid Vapor Pressure Apparatus (RVP 100) was developed to save operator's time in carrying out vapor pressure testing of gasoline, to reduce the variables inherent in the standard method, and to improve repeatability of test results. The standard American Society of Testing Materials (ASTM) test methods D323 and D4953 specify that a standard gasoline chamber, sometimes referred to as a "test bomb", is filled with a chilled sample connected to an air chamber, and immersed in a constant temperature bath at 100° F. The apparatus is periodically removed from the bath and shaken until a constant pressure is observed on a gauge attached to the air chamber. After each test, gauge calibration must be checked, with the total test time involved typically being on the order of 20-30 minutes.

A later Reid Vapor Pressure Apparatus was developed to meet the requirements of ASTM standard test methods D323 and D4953, in which the standard gasoline chambers filled with the sample to be tested are coupled to air chambers as specified in the aforementioned test methods to form a vapor pressure "bomb". The assembled vapor pressure bombs are then tilted 20° to 30° with the upper end extending downward to transfer some of the sample into the vapor chamber. The test bomb is then placed horizontally in a constant temperature bath and rotated slowly in 180° clockwise and 180° counterclockwise cycles about its longitudinal axis. Although this has shortened the period for achieving thermal equilibrium, it has also resulted in gasoline flowing into the tube leading to the pressure gauge which interferes with and limits the accuracy of the vapor pressure measurements.

The present invention overcomes the aforementioned limitations of the prior art by providing apparatus for measuring the vapor pressure of a volatile liquid which continuously shakes one or more pressure test chambers in a constant temperature bath by moving a tray on which the test chambers are positioned in a reciprocating manner. There is no need for the operator to tilt the test chambers downward to insure sample transfer from the liquid chamber to the vapor chamber. The test chamber is placed horizontally in a constant temperature bath. Some of the sample is transferred from the liquid chamber to the vapor chamber during vigorous reciprocating movement of the test chambers during the test. Handling of the pressure test chambers during testing is eliminated, freeing an operator to perform other work after the test is initiated. Thermal equilibrium is achieved in a very short time, expediting vapor pressure testing, and the liquid under test remains isolated from the pressure transducer.

Accordingly, it is an object of the present invention to provide improved apparatus for measuring the vapor pressure of a volatile liquid.

Yet another object of the present invention is to quickly and accurately measure the vapor pressure of a volatile petroleum product such as gasoline at a predetermined, fixed temperature and using conventional test chambers in accordance with ASTM standard test methods, D323, D4953.

A further object of the present invention is to quickly bring a liquid in a closed chamber to a fixed, predetermined temperature for measuring the vapor pressure of the liquid at the predetermined temperature.

The present invention contemplates apparatus for measuring the vapor pressure of a volatile liquid comprising: one or more closed test chambers each including a first section containing a liquid and a second section coupled to the first section; a constant temperature source coupled to the test chambers for maintaining the liquid in each of the test chambers at a predetermined, fixed temperature; a moveable tray coupled to the test chambers; drive means coupled to the moveable tray for linearly displacing the moveable tray and the test chambers in a reciprocating manner for transferring a portion of the liquid from the first section to the second section of each of the test chambers and for rapidly bringing the temperature of the liquid to the predetermined, fixed temperature in stabilizing the vapor pressure of the liquid at a constant value; and vapor pressure measuring and indicator means coupled to the second section of each of the test chambers and responsive to the vapor pressure of the liquid therein for displaying the vapor pressure of the liquid at the predetermined, fixed temperature.

BRIEF DESCRIPTION OF THE DRAWING

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DETAILED DESCRIPTION OF THE PREFERRED EMBODIMENT

Figure 1:
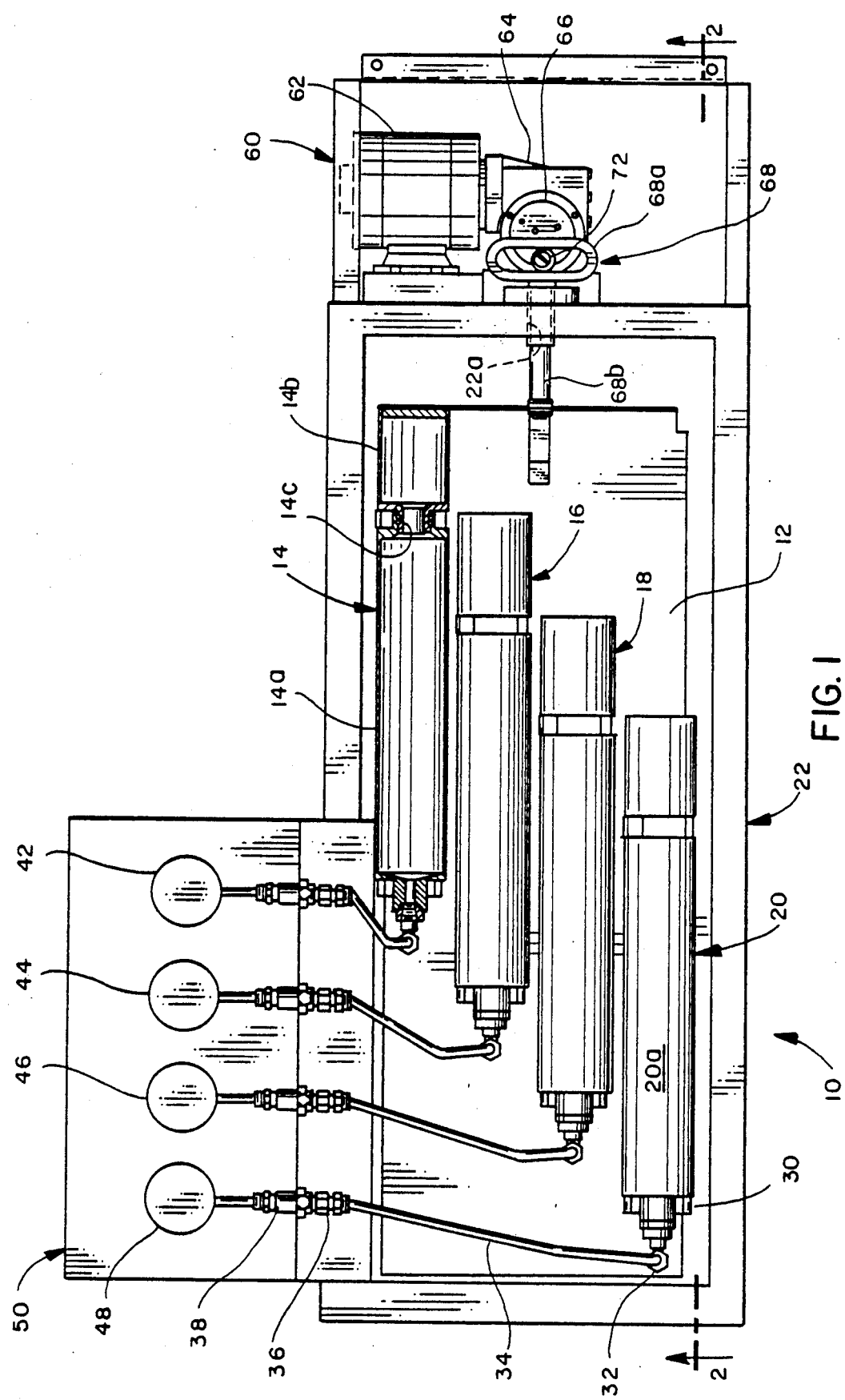
FIG. 1 is a top plan view of apparatus for measuring the vapor pressure of a volatile liquid in accordance with the present invention.
Figure 2:
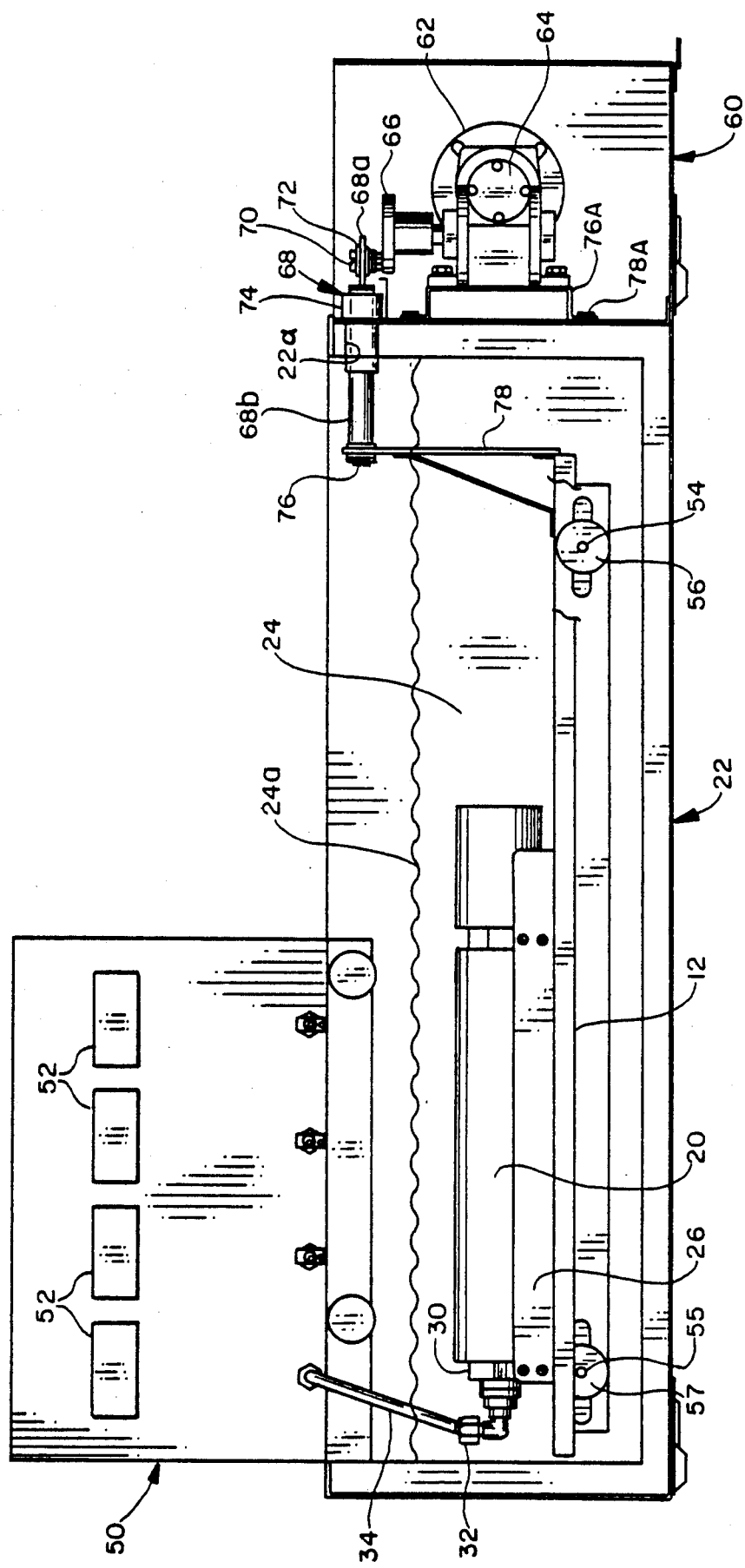
FIG. 2 is a lateral sectional view of the vapor pressure measuring apparatus of FIG. 1 taken along site line 2—2 therein.

Referring to FIG. 1, there is shown a top plan view of a vapor pressure measuring apparatus 10 in accordance with the principles of the present invention. FIG. 2 is a lateral sectional view of the vapor pressure measuring apparatus of FIG. 1 taken along side line 2—2 therein. The vapor pressure measuring apparatus 10 includes a water bath 22 having an open upper portion and a bottom and four sides. Disposed within the water bath 22 is a moveable tray 12. Positioned upon and coupled to the generally planar moveable tray 12 are first, second, third and fourth test chambers, or pressure bombs, 14, 16, 18 and 20. As shown for the case of the first test chamber 14, each of the test chambers includes a vapor compartment 14a and a liquid compartment 14b which are coupled by means of a narrow channel 14c. Each of the aforementioned test chambers is positioned upon and securely mounted to the tray 12 by means of a respective mounting bracket, which for the case of the fourth test chamber 20 is shown as element 26 in FIG. 2.

A pair of stationary shafts 54 and 55 are attached to an inner portion of the water bath 22 and are positioned beneath the tray 12. Disposed on respective ends of the first stationary bath 54 are a first pair of wheels 56, while positioned on respective ends of the second shaft 55 are a second pair of wheels 57, wherein only one of each pair of the wheels is shown in the FIG. 2 for simplicity. Each pair of wheels 56, 57 is further positioned in contact with a lower portion of the tray 12 for providing support for the tray. The wheels 56 and 57 in contact with the lower portion of the tray 12 allow the tray to be linearly displaced in a direction along its length. The bath 22 is filled with water 24 maintained at a predetermined, constant temperature to a level indicated by numeral 24a.

A distal end of the vapor compartment portion of each of the test chambers is coupled to an elongated tube 34 by means of a coupler 32 as shown for the fourth test chamber 20 in FIG. 1. A vapor chamber clamp 30 disposed intermediate the distal end of the vapor compartment 20a of the fourth test chamber 20 and the coupler 32 provides a tight gas seal on the end of the test chamber. The other end of the elongated tube 34 is coupled by means of the combination of a shut-off valve 36 and a coupling body 38 to a fourth pressure transducer, or manometer, 48. The first, second and third test chambers 14, 16 and 18 are each similarly coupled to first, second and third pressure transducers 42, 44 and 46, respectively. Each of the aforementioned pressure transducers in a temperature controlled environment is coupled to a respective one of a plurality of digital displays 52 for providing a signal representing the vapor pressure within a test chamber for viewing on the digital display. The combination of first, second, third and fourth pressure transducers 42, 44, 46 and 48 and the digital displays 52 form a Reid vapor pressure measuring and indicator arrangement 50.

Mounted to one end of the tray 12 by conventional means such as a coupling bracket 78 and a bolt 76 is a drive assembly 60. The drive assembly includes a motor 62 which is coupled to an eccentric 66 by means of a gear box, or transmission, 64. Mounted to an upper surface of the eccentric 66 by means of a screw 70 is a ball bearing 72. Engaging the ball bearing 72 is an oval ring 68a of a push rod assembly 68. The push rod assembly 68 further includes a rod 68b coupled to the oval ring 68a and extending through an aperture 22a in a lateral wall of the water bath 22. A bearing 74 disposed about the rod 68b facilitates its linear displacement within the aperture 22a in the water bath 22. A distal end of the rod 68b is coupled by means of bolt 76 to the generally upright coupling bracket 78 which is securely attached to an end of the moveable tray 12.

Rotation of the eccentric 66 by means of the motor 62 via the gear box 64 causes the ball bearing 72 within the oval ring 68 to traverse a circular path. This causes the oval ring 68 as well as the rod 68b attached thereto to be linearly displaced through the aperture 22a in the water bath 22 in a reciprocating manner. The tray 12 coupled to the rod 68b as well as the first, second, third and fourth test chambers 14, 16, 18 and 20 positioned on the tray are similarly displaced in the water 24 in a reciprocating manner. With the water maintained at a constant temperature, this reciprocating displacement of the test chambers along their respective longitudinal axes causes a portion of the liquid within the liquid compartment of the test chamber to be transferred to its vapor compartment and to rapidly reach a constant vapor pressure determined by the temperature of the water bath.

There has thus been shown an apparatus for measuring the vapor pressure of volatile liquids in one or more cylindrical test chambers immersed in a constant temperature water bath. Each test chamber includes coupled liquid and vapor compartments, with the vapor compartment of each test chamber further coupled to a pressure transducer and display arrangement. The test chambers are mounted on a moveable tray within the constant temperature water bath. An eccentric drive assembly driven by the combination of a motor and gear box is coupled to the tray for linearly displacing the tray and test chambers mounted thereto in a reciprocating manner until a constant pressure within the test chambers is observed on the vapor pressure display.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. Apparatus for measuring vapor pressure of a volatile liquid, said apparatus comprising:
    a closed test chamber including a first section containing the liquid and a second section coupled to said first section;
    a constant temperature source for receiving said test chamber and for bringing said test chamber and said liquid to a predetermined, fixed temperature;
    a moveable tray for holding said test chamber;
    drive means coupled to said moveable tray for linearly displacing said moveable tray and said test chamber in a reciprocating manner for transferring a portion of the liquid from the first section to the second section of said test chamber and for rapidly bringing the temperature of the liquid to said predetermined, fixed temperature and stabilizing the vapor pressure of the liquid at a constant value; and
    vapor pressure measuring and indicator means coupled to the second section of said test chamber and responsive to the vapor pressure of the liquid therein for measuring and displaying the vapor pressure of the liquid at said predetermined, fixed temperature; whereby said liquid may be placed in said first section of said test chamber and said reciprocating motion of said drive means will transfer at least some of said liquid to said second section of said test chamber and thereby obviate any need to manually effect a transfer of liquid from said first chamber to said second chamber.

2. The apparatus of claim 1 wherein said constant temperature source comprises a water bath.

3. The apparatus of claim 2 wherein said test chamber and said moveable tray are disposed within said water bath.

4. The apparatus of claim 3 further comprising rotational support means disposed between said water bath and said moveable tray for providing support for said moveable tray.

5. The apparatus of claim 4 wherein said rotational support means includes a plurality of wheels.

6. The apparatus of claim 1 wherein said vapor pressure measuring and indicator means is mounted to said moveable tray.

7. The apparatus of claim 1 wherein said vapor pressure measuring and indicator means includes a digital display.

8. The apparatus of claim 1 wherein said pressure measuring and indicator means includes a pressure transducer.

9. The apparatus of claim 1 wherein said drive means includes a rotary motor and an eccentric drive assembly for converting rotational displacement of said motor to reciprocating linear displacement.

10. The apparatus of claim 9 wherein said drive means further includes, in combination, an eccentric coupled to said motor and a reciprocating push rod coupled to said moveable tray.

11. The apparatus of claim 10 wherein said drive means further includes an oval ring coupled to said push rod and to said eccentric, and wherein the combination of said oval ring and said push rod is linearly displaced in a reciprocating manner by said eccentric.

12. The apparatus of claim 10 wherein said drive means further includes a gear box coupled between said motor and said eccentric.

13. The apparatus of claim 1 further comprising a plurality of test chambers coupled to said constant temperature source and mounted to said moveable tray, said apparatus further comprising a plurality of vapor pressure measuring and indicator means each coupled to a respective one of said plurality of test chambers.

* * * * *